US00PP19889P2

(12) United States Plant Patent
Hambali

(10) Patent No.: US PP19,889 P2
(45) Date of Patent: Apr. 7, 2009

(54) ***AGLAONEMA* PLANT NAMED 'TWYAG0031'**

(50) Latin Name: *Aglaonema hybrida*
Varietal Denomination: TWYAG0031

(75) Inventor: Gregori Garnadi Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/906,500

(22) Filed: Oct. 2, 2007

(51) Int. Cl.
*A01H 5/00* (2006.01)

(52) U.S. Cl. ..... Plt./376

(58) Field of Classification Search ..... Plt./376
See application file for complete search history.

*Primary Examiner*—Annette H Para
*Assistant Examiner*—S. B. McCormick Ewoldt
(74) *Attorney, Agent, or Firm*—Jondle & Associates, P.C.

(57) ABSTRACT

A new *Aglaonema* plant particularly distinguished by having foliage that is dark green and abundantly marked with pale pink spots and coalescing blotches, primary veins that are white and flushed with pale pink, midribs that are white and variably tinged with pale pink, a short, densely leafy, compact and mounded plant habit and yellow-green spathes spotted with white, is disclosed.

1 Drawing Sheet

Genus and species: *Aglaonema hybrida.*
Variety denomination: 'TWYAG0031'.

BACKGROUND OF THE NEW PLANT

The present invention comprises a new and distinct cultivar of *Aglaonema,* botanically known as *Aglaonema hybrida* and hereinafter referred to by the variety name as 'TWYAG0031'. The new variety originated from an open pollination made in Bogor, West Java, Indonesia between unknown individual plants of *Aglaonema* (species unknown). The new variety was discovered as a single plant within the progeny of the stated open pollination in a controlled environment in Bogor, West Java, Indonesia.

The new variety was created in Bogor, West Java, Indonesia and has been repeatedly asexually reproduced by vegetative cuttings and tissue culture in Apopka, Fla. for two or more generations. The present invention has been found to retain its distinctive characteristics through successive asexual propagations.

SUMMARY OF THE INVENTION

The following are the most outstanding and distinguishing characteristics of the new variety when grown under normal horticultural practices in Apopka, Fla.

1. Foliage is dark green and abundantly marked with pale pink spots and coalescing blotches;
2. The primary veins are white and flushed with pale pink;
3. The midrib is white and variably tinged with pale pink;
4. A short, densely leafy, compact and mounded plant habit; and
5. Yellow-green spathes spotted with white.

DESCRIPTION OF THE PHOTOGRAPH

This new *Aglaonema* plant is illustrated by the accompanying photograph which shows the overall plant habit. The colors shown are as true as can be reasonably obtained by conventional photographic procedures. The photograph is of a 12-month old plant.

DESCRIPTION OF THE NEW VARIETY

The following detailed description sets forth the distinctive characteristics of 'TWYAG0031'. The data which define these characteristics were collected from asexual reproductions carried out in Apopka, Fla. The plant history was taken on 12 month-old plants started from a single four-leaf rooted cutting, still in a vegetative state and grown in Apopka, Fla. Rooted cuttings were planted in 20 cm pots and grown in a greenhouse in February 2007. The plants were pinched twice. Color readings were taken under natural light. Color references are primarily to the R.H.S. Colour Chart of The Royal Horticultural Society of London (RHS) (2001).

DETAILED BOTANICAL DESCRIPTION

Classification:
- *Family.*—Araceae.
- *Botanical.*—*Aglaonema hybrida.*
- *Common.*—Chinese Evergreen.

Growth:
- *Form.*—Short, compact, dense and a mounded shape; wider than tall Growth and branching habit: Small in stature; densely leafy and compact; new leaves emerge straight and upright and mature leaves lean outward.
- *Height* (*from soil to top of leaf plane*).—18 cm to 21 cm.
- *Diameter* (*area of spread, as measured from leaf tip to leaf tip across the canopy*).—35 cm to 40 cm.
- *Growth rate.*—Typical of commercial *Aglaonema* varieties.
- *Vigor.*—Plants produce axillary branches and numerous leaves; consistent progressive growth.
- *Time to produce a finished flowering plant.*—About 12 months starting from a single 4-leaf rooted cutting with the plants pinched twice in 15 cm to 20 cm pots.

*Root description.*—Thick, fleshy and white with finer lateral branches.

*Number of divisions or clumps per year.*—About eight 4-leaf cuttings per year.

*Durability of foliage to stresses.*—Foliage holds up well against damage from shipping and handling; plants are durable and have excellent indoor keeping quality.

*High temperature tolerance.*—About 104° F. for several hours without damage.

*Low temperature tolerance.*—About 55° F. for several hours without damage.

Stems:

*Number of branches per plant.*—About 25

*Type of branching.*—Basal

*Length (from soil line to junction of the newest two leaves).*—5 cm to 8 cm

*Diameter (measured from the midpoint).*—0.75 cm

*Internode length.*—0.45 cm to 0.7 cm

*Color.*—Immature: Between RHS 144B to RHS 144C and tinged with RHS 146C. Mature: RHS 146B tinged with RHS 151C. Oldest stems: Between RHS147A to RHS147B.

*Shape and appearance.*—Columnar, cylindrical and upright.

*Aspect.*—Vertical, upright or leaning outward about 30 degrees to 40 degrees; the apex of the stem is often turned up.

*Strength.*—Sturdy and somewhat flexible.

*Axillary buds.*—Shape: Elliptic to ovate, flat to convex. Length: 0.22 cm. Width: 0.12 cm. Color: RHS 145C.

Leaves:

*Arrangement.*—Alternate and simple; the leaves are oriented opposite along the stem; the leaf blade folds upward along the midrib.

*Quantity of leaves per stem.*—9.

*Immature leaf (newly expanded leaf).*—Color: Upper surface: Base color is darker and greener than but closest to RHS 147A and marked with colors between RHS 56A to RHS 56B spots and coalescing blotches Lower surface: Base color is RHS 147B and tinged with RHS 55C; the upper surface patterns and markings are visible through to the lower surface of the leaf; the leaf blade is marked with RHS 55C spots and coalescing blotches.

*Mature leaf.*—Color: Upper surface: Base color is darker than but closest to RHS 147A and marked with RHS 56B to RHS 56D spots and coalescing blotches Lower surface: Base color is between RHS 147A to RHS 147B and tinged with RHS 55C; the upper surface patterns and markings are visible through to the lower surface of the leaf; the leaf blade is marked with spots and coalescing blotches between RHS 55C to RHS 56A.

*Length.*—8.3 cm to 10.4 cm.

*Width.*—Flattened: 7.0 cm to 10.5 cm. Not flattened: 6.8 cm to 9.5 cm.

*Shape.*—Round to broadly ovate.

*Apex.*—Cuspidate.

*Base.*—Obtuse to slightly cordate.

*Margin.*—Smooth and entire with some broad undulations.

*Appearance (both surfaces).*—Smooth and leathery; new leaves are shiny and mature leaves are glossy to dull; the leaf blade is convex between the main veins and somewhat puckered along the midrib resulting in a textured appearances.

*Pubescence (both surfaces).*—Absent.

*Venation pattern.*—Pinnate.

*Venation color.*—Immature leaf (newly expanded leaf): Upper surface: Primary veins: RHS155C and tinged with RHS 56C. Midrib: RHS155C and tinged with RHS 56C. Lower surface: Primary veins: RHS 145D and tinged with RHS 56A. Midrib: the proximal end is between RHS 147B to RHS 146B and tinged with RHS 145D and the distal end is RHS 155C and tinged with RHS 56D. Mature leaf: Upper surface: Primary veins: RHS155C and tinged with RHS 56B. Midrib: the proximal end is RHS 192D and the distal end is RHS 56B. Lower surface: Primary veins: RHS 145D and tinged with RHS 56B. Midrib: the proximal end is between RHS 147C to RHS 146B and the distal end is RHS 155C.

Petioles:

*Aspect.*—Vertical and upright when newly expanded and becoming curved outward to about 30 degrees with maturity.

*Length.*—5.4 cm.

*Diameter.*—Distal: 0.25 cm. Proximal (petiole and petiole sheath clasps the stem proximally): Flattened: 2.7 cm. Not flattened: 0.60 cm. Depth: 0.75 cm.

*Color.*—Distal (between the top of the wing and the base of the leaf): the distal end is between RHS 147A to RHS 147B. Proximal: RHS 147B and tinged with RHS 146C Areas adjacent to the stem: Between RHS 158D to RHS 145D.

*Wing.*—Length: 2.4 cm to 3.8 cm. Diameter: Midpoint: 0.6 cm. Base: 0.75 cm. Depth: 0.6 cm. Color: Inside: RHS 155D and tinged with RHS 148D. Outside: RHS 147A and tinged with RHS146C, the margin is tinged with RHS 49B. Area adjacent to the stem: Between RHS 158D to RHS 145D.

*Cataphylls.*—Length: 3.5 cm to 4.7 cm. Width: 1.6 cm. Shape: Lanceolate, keeled and translucent. Apex: Cuspidate. Base: Clasps the stem. Color: Inside: The distal end is between RHS 148D to RHS 147C and the proximal end is RHS 148D with the center being tinged with RHS 49B. Outside: The distal end is between RHS 147B to RHS 146B and the proximal end is between RHS 147C to RHS 147D and the keel is tinged with RHS 49B.

Inflorescence:

*Appearance.*—Hooded spathes surrounding a columnar spadix are borne atop an upright peduncle; monoecious; the spadix is a central column of sessile, simple male and female flowers separated into two zones; the male flowers occupy the upper three-fourths of the spadix while the female flowers occupy the lower one-fourth of the spadix.

*Quantity of inflorescences per stem.*—About 1.

*Quantity of inflorescences per plant.*—About 9.

*Aspect.*—Upright.

*Height (from base of peduncle to tip of spathe).*—8.3 cm.

*Diameter/width.*—1.2 cm.

*Flowering habit.*—Seasonal; the natural flowering season is fall to winter as observed in Apopka, Fla. the flowers are persistent.

*Fragrance.*—Absent.

*Ratio of inflorescence to opening.*—About 1 new flower every 21 days.

*Peduncle.*—Length: 7.5 cm. Diameter: 0.25 cm. Aspect: Upright. Strength: Sturdy and flexible. Color: RHS 147A to RHS 147B.

Spathe:

*Appearance.*—Simple, hooded, cupped and enclosing the spadix; both surfaces are smooth and shiny.

*Aspect.*—Upright.

*Shape.*—Elliptic.

*Apex.*—Cuspidate.

*Margin.*—Entire.

*Pubescence* (*both inner and outer surfaces*).—Absent.

*Size.*—Length: 3.7 cm. Width: 1.2 cm (not flattened).

*Color* (*when opening*).—Front side: RHS 147C. Rear side: Between RHS 146B to RHS 146C and spotted with RHS 145D.

*Color* (*fully opened*).—Front side: Between RHS 147C to RHS 147D. Rear side: Between RHS 147A to RHS 147B, RHS 146B and spotted with RHS 155B.

*Color* (*fading to*).—RHS 200B.

Spadix:

*Appearance and shape.*—Columnar.

*Aspect.*—Upright.

*Size.*—Length: 2.2 cm. Diameter of the female zone: 0.6 cm. Diameter of the male zone: 0.8 cm. Length of the female zone: 0.3 cm. Length of the male zone: 1.9 cm.

*Apex.*—Obtuse.

*Base.*—Obtuse.

*Margin.*—Pebbled.

*Color.*—Female zone (immature): RHS 8C. Male zone (immature): RHS 11D. Female zone (mature): RHS 10C. Male zone (mature): RHS 8D.

Flowers:

*Type.*—Simple.

*Quantity of female flowers per spadix.*—10.

*Quantity of male flowers per spadix.*—180.

*Shape of female.*—Elliptic.

*Shape of male.*—Obovate, inverted triangle.

*Size.*—Female width: 0.1 cm. Male width: 0.1 cm. Female height and depth: 0.2 cm. Male height and depth: 0.2 cm.

Reproductive organs:

*Anther color.*—RHS 8D.

*Pollen amount.*—Not observed.

*Stigma color.*—RHS 10C.

*Ovary color.*—RHS 145D.

Fruit and seed set: None observed.

Disease and insect resistance: Typical of *Aglaonema* species; no particular susceptibility or resistance to pests or diseases noted.

COMPARISON WITH KNOWN VARIETIES

'TWYAG0031' differs from the commercial variety 'Key Largo' (U.S. Plant Pat. No. 17,550) in that 'TWYAG0031'has foliage with pale pink spots and blotches with round to broadly ovate leaves, while 'Key Largo' has foliage with silver flecks and spots and oblong leaves.

'TWYAG0031' differs from the commercial variety 'TWYAG0003' (U.S. Plant Pat. No. 17,673) in that 'TYWAG0031' has yellow-green petioles, while 'TWYAG0003' has pink petioles.

I claim:

1. A new and distinct cultivar of *Aglaonema* plant as shown and described herein.

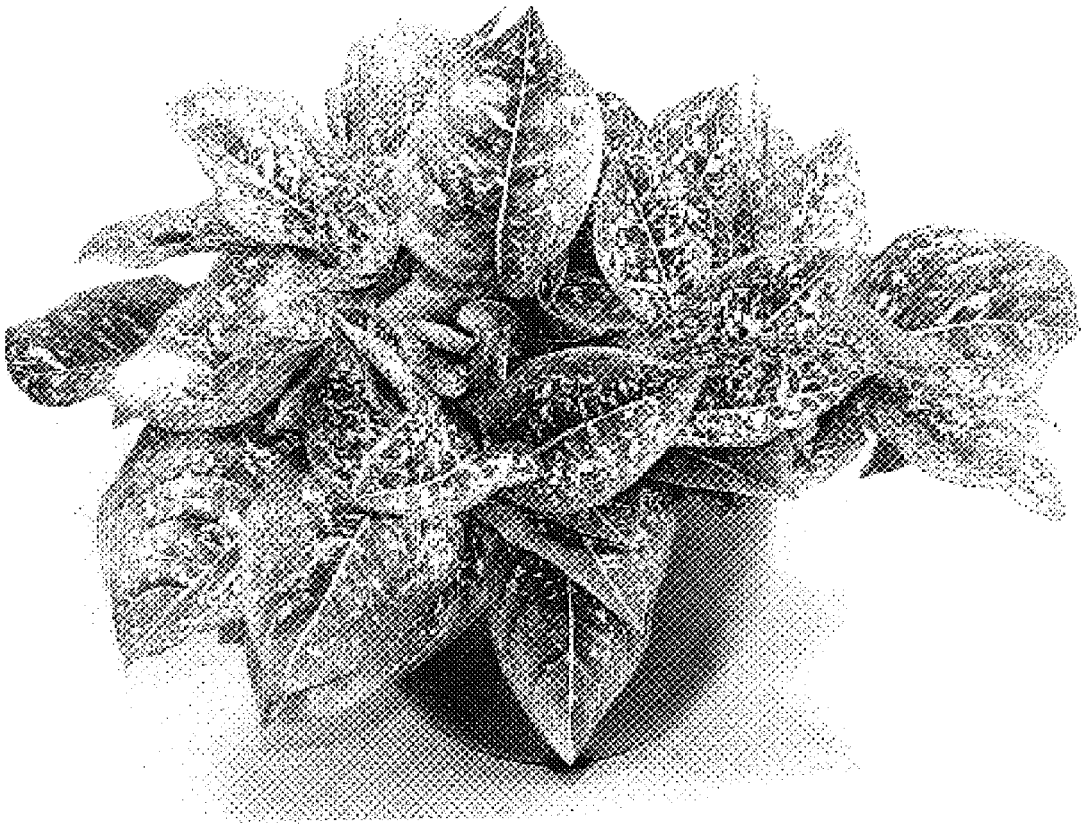

* * * * *